(12) United States Patent
Houser et al.

(10) Patent No.: US 9,649,150 B2
(45) Date of Patent: May 16, 2017

(54) SELECTIVE ACTIVATION OF ELECTRONIC COMPONENTS IN MEDICAL DEVICE

(75) Inventors: Kevin L. Houser, Springboro, OH (US); Foster B. Stulen, Mason, OH (US)

(73) Assignee: Ethicon Endo-Surgery, LLC, Guaynabo, PR (US)

(*) Notice: Subject to any disclaimer, the term of this patent is extended or adjusted under 35 U.S.C. 154(b) by 0 days.

(21) Appl. No.: 13/276,707

(22) Filed: Oct. 19, 2011

(65) Prior Publication Data

US 2012/0116366 A1    May 10, 2012

Related U.S. Application Data

(60) Provisional application No. 61/410,603, filed on Nov. 5, 2010, provisional application No. 61/487,846, filed on May 19, 2011.

(51) Int. Cl.
*A61B 18/12* (2006.01)
*A61B 18/14* (2006.01)
(Continued)

(52) U.S. Cl.
CPC .... *A61B 18/1442* (2013.01); *A61B 17/00234* (2013.01); *A61B 17/2812* (2013.01); *A61B 17/320068* (2013.01); *A61B 17/320092* (2013.01); *A61B 18/00* (2013.01); *A61B 18/04* (2013.01); *A61B 18/12* (2013.01); *A61B 18/14* (2013.01); *A61B 18/1445* (2013.01); *A61N 7/00* (2013.01); *H02J 7/0045* (2013.01); *A61B 17/064* (2013.01); *A61B 17/285* (2013.01);
(Continued)

(58) Field of Classification Search
CPC ............ A61B 18/1442; A61B 18/1445; A61B 2017/00876; A61B 2018/00922
USPC ....................................... 606/1, 41
See application file for complete search history.

(56) References Cited

U.S. PATENT DOCUMENTS 1,754,806 A    4/1930    Stevenson
3,297,192 A    1/1967    Swett
(Continued)

FOREIGN PATENT DOCUMENTS

DE    102008051866    10/2010
DE    102009013034    10/2010
(Continued)

OTHER PUBLICATIONS

International Search Report and Written Opinion dated Jan. 26, 2012 for Application No. PCT/US2011/059212.
(Continued)

*Primary Examiner* — Aaron Roane
(74) *Attorney, Agent, or Firm* — Frost Brown Todd LLC

(57) ABSTRACT

A surgical instrument comprises a body, a transmission assembly, and a switch. The body comprises a control unit and an integral power source. The power source is operable to selectively deliver power to the control unit. The transmission assembly extends distally from the body. The transmission assembly also includes an end effector driven by the control unit. The switch is in communication with the control unit and the power source. The transmission assembly is operable to actuate the switch to enable delivery of power from the power source to the control unit.

12 Claims, 11 Drawing Sheets

(51) Int. Cl.
*A61B 17/00* (2006.01)
*A61B 17/32* (2006.01)
*A61B 18/00* (2006.01)
*A61B 18/04* (2006.01)
*H02J 7/00* (2006.01)
*A61B 17/28* (2006.01)
*A61N 7/00* (2006.01)
*H01M 2/26* (2006.01)
*H01M 2/10* (2006.01)
*A61B 90/00* (2016.01)
*A61B 17/064* (2006.01)
*A61B 17/285* (2006.01)
*A61B 17/29* (2006.01)
*A61B 34/00* (2016.01)
*A61B 90/40* (2016.01)

(52) U.S. Cl.
CPC ........ *A61B 18/1206* (2013.01); *A61B 18/1233* (2013.01); *A61B 34/25* (2016.02); *A61B 90/40* (2016.02); *A61B 2017/0046* (2013.01); *A61B 2017/00084* (2013.01); *A61B 2017/00398* (2013.01); *A61B 2017/00473* (2013.01); *A61B 2017/00477* (2013.01); *A61B 2017/00482* (2013.01); *A61B 2017/00734* (2013.01); *A61B 2017/291* (2013.01); *A61B 2017/293* (2013.01); *A61B 2017/294* (2013.01); *A61B 2017/2929* (2013.01); *A61B 2017/2931* (2013.01); *A61B 2017/2933* (2013.01); *A61B 2018/0019* (2013.01); *A61B 2018/00178* (2013.01); *A61B 2018/00791* (2013.01); *A61B 2018/00988* (2013.01); *A61B 2018/1226* (2013.01); *A61B 2018/1412* (2013.01); *A61B 2018/1455* (2013.01); *A61B 2090/0803* (2016.02); *A61B 2090/0813* (2016.02); *A61B 2090/0814* (2016.02); *H01M 2/10* (2013.01); *H01M 2/26* (2013.01); *Y10T 29/49005* (2015.01); *Y10T 29/49895* (2015.01); *Y10T 29/53913* (2015.01)

(56) References Cited

U.S. PATENT DOCUMENTS

| | | |
|---|---|---|
| 3,419,198 A | 12/1968 | Pettersen |
| 3,619,671 A | 11/1971 | Shoh |
| 4,034,762 A | 7/1977 | Cosens et al. |
| 4,057,220 A | 11/1977 | Kudlacek |
| 4,535,773 A | 8/1985 | Yoon |
| 4,641,076 A | 2/1987 | Linden et al. |
| 4,662,068 A | 5/1987 | Polonsky |
| 4,666,037 A | 5/1987 | Weissman |
| 4,685,459 A | 8/1987 | Koch et al. |
| 4,717,018 A | 1/1988 | Sacherer et al. |
| 4,717,050 A | 1/1988 | Wright |
| 4,721,097 A | 1/1988 | D'Amelio |
| 4,768,969 A | 9/1988 | Bauer et al. |
| 4,800,878 A | 1/1989 | Cartmell |
| 4,844,259 A | 7/1989 | Glowczewskie, Jr. |
| 4,878,493 A | 11/1989 | Pasternak et al. |
| 5,071,417 A | 12/1991 | Sinofsky |
| 5,107,155 A | 4/1992 | Yamaguchi |
| 5,144,771 A | 9/1992 | Miwa |
| 5,169,733 A | 12/1992 | Savovic et al. |
| 5,176,677 A | 1/1993 | Wuchinich |
| 5,246,109 A | 9/1993 | Markle et al. |
| 5,273,177 A | 12/1993 | Campbell |
| 5,277,694 A | 1/1994 | Leysieffer et al. |
| 5,306,282 A * | 4/1994 | Muller ............ A61B 17/320068 606/167 |
| 5,308,358 A | 5/1994 | Bond et al. |
| 5,322,055 A | 6/1994 | Davison |
| 5,339,799 A | 8/1994 | Kami et al. |
| 5,358,508 A | 10/1994 | Cobb et al. |
| 5,361,902 A | 11/1994 | Abidin et al. |
| 5,429,229 A | 7/1995 | Chester et al. |
| 5,449,370 A | 9/1995 | Vaitekunas |
| 5,454,378 A | 10/1995 | Palmer et al. |
| 5,501,607 A | 3/1996 | Yoshioka et al. |
| 5,507,297 A | 4/1996 | Slater et al. |
| 5,561,881 A | 10/1996 | Klinger et al. |
| 5,578,052 A | 11/1996 | Koros et al. |
| 5,580,258 A | 12/1996 | Wakata |
| 5,582,617 A | 12/1996 | Klieman et al. |
| 5,590,778 A | 1/1997 | Dutchik |
| 5,592,065 A | 1/1997 | Oglesbee et al. |
| 5,597,531 A | 1/1997 | Liberti et al. |
| 5,599,350 A | 2/1997 | Schulze et al. |
| 5,630,420 A | 5/1997 | Vaitekunas |
| 5,630,456 A | 5/1997 | Hugo et al. |
| 5,690,222 A | 11/1997 | Peters |
| 5,707,369 A | 1/1998 | Vaitekunas et al. |
| 5,741,305 A | 4/1998 | Vincent et al. |
| 5,776,155 A | 7/1998 | Beaupre et al. |
| 5,800,336 A | 9/1998 | Ball et al. |
| 5,817,128 A | 10/1998 | Storz |
| 5,868,244 A | 2/1999 | Ivanov et al. |
| 5,873,873 A | 2/1999 | Smith et al. |
| 5,882,310 A | 3/1999 | Marian, Jr. |
| 5,935,144 A | 8/1999 | Estabrook |
| 5,938,633 A | 8/1999 | Beaupre |
| 5,944,737 A | 8/1999 | Tsonton et al. |
| 5,951,575 A | 9/1999 | Bolduc et al. |
| 5,980,510 A | 11/1999 | Tsonton et al. |
| 5,997,531 A | 12/1999 | Loeb et al. |
| 6,018,227 A | 1/2000 | Kumar et al. |
| 6,051,010 A | 4/2000 | Dimatteo et al. |
| 6,056,735 A | 5/2000 | Okada et al. |
| 6,063,098 A | 5/2000 | Houser et al. |
| 6,066,151 A | 5/2000 | Miyawaki et al. |
| 6,083,191 A | 7/2000 | Rose |
| 6,083,223 A | 7/2000 | Baker |
| 6,099,537 A | 8/2000 | Sugai et al. |
| 6,113,593 A | 9/2000 | Tu et al. |
| 6,123,702 A | 9/2000 | Swanson et al. |
| 6,142,997 A | 11/2000 | Michelson |
| 6,165,191 A | 12/2000 | Shibata et al. |
| 6,190,386 B1 * | 2/2001 | Rydell ............... 606/51 |
| 6,204,592 B1 | 3/2001 | Hur |
| 6,214,023 B1 | 4/2001 | Whipple et al. |
| 6,246,896 B1 | 6/2001 | Dumoulin et al. |
| 6,248,238 B1 | 6/2001 | Burtin et al. |
| 6,287,304 B1 | 9/2001 | Eggers et al. |
| 6,325,811 B1 | 12/2001 | Messerly |
| 6,339,368 B1 | 1/2002 | Leith |
| 6,398,755 B1 | 6/2002 | Belef et al. |
| 6,409,742 B1 | 6/2002 | Fulton, III et al. |
| 6,500,176 B1 | 12/2002 | Truckai et al. |
| 6,500,188 B2 | 12/2002 | Harper et al. |
| 6,514,267 B2 | 2/2003 | Jewett |
| 6,517,561 B1 * | 2/2003 | Phillips ............... 606/180 |
| 6,520,185 B1 | 2/2003 | Bommannan et al. |
| 6,561,983 B2 | 5/2003 | Cronin et al. |
| 6,609,414 B2 | 8/2003 | Mayer et al. |
| 6,622,731 B2 | 9/2003 | Daniel et al. |
| 6,623,500 B1 | 9/2003 | Cook et al. |
| 6,626,901 B1 | 9/2003 | Treat et al. |
| 6,647,281 B2 | 11/2003 | Morency |
| 6,650,975 B2 | 11/2003 | Ruffner |
| 6,656,177 B2 | 12/2003 | Truckai et al. |
| 6,658,301 B2 | 12/2003 | Loeb et al. |
| 6,666,875 B1 | 12/2003 | Sakurai et al. |
| 6,717,193 B2 | 4/2004 | Olewine et al. |
| 6,730,042 B2 | 5/2004 | Fulton et al. |
| 6,758,855 B2 | 7/2004 | Fulton, III et al. |
| 6,761,698 B2 | 7/2004 | Shibata et al. |
| 6,761,701 B2 | 7/2004 | Cucin |
| 6,783,524 B2 | 8/2004 | Anderson et al. |
| 6,815,206 B2 | 11/2004 | Lin et al. |
| 6,821,671 B2 | 11/2004 | Hinton et al. |
| 6,838,862 B2 | 1/2005 | Luu |

(56) References Cited

U.S. PATENT DOCUMENTS

| | | |
|---|---|---|
| 6,860,880 B2 | 3/2005 | Treat et al. |
| 6,869,435 B2 | 3/2005 | Blake |
| 6,923,807 B2 | 8/2005 | Ryan et al. |
| 6,982,696 B1 | 1/2006 | Shahoian |
| 7,031,155 B2 | 4/2006 | Sauciuc et al. |
| 7,077,853 B2 | 7/2006 | Kramer et al. |
| 7,083,589 B2 | 8/2006 | Banko et al. |
| 7,101,371 B2 | 9/2006 | Dycus et al. |
| 7,112,201 B2 | 9/2006 | Truckai et al. |
| 7,125,409 B2 | 10/2006 | Truckai et al. |
| 7,150,712 B2 | 12/2006 | Buehlmann et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckal et al. |
| 7,364,061 B2 | 4/2008 | Swayze et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,563,142 B1 | 7/2009 | Wenger et al. |
| 7,583,564 B2 | 9/2009 | Ketahara et al. |
| 7,638,958 B2 | 12/2009 | Philipp et al. |
| 7,643,378 B2 | 1/2010 | Genosar |
| 7,717,312 B2 | 5/2010 | Beetel |
| 7,721,936 B2 | 5/2010 | Shelton, IV et al. |
| 7,738,971 B2 | 6/2010 | Swayze et al. |
| 7,766,910 B2 | 8/2010 | Hixson et al. |
| 7,766,929 B2 | 8/2010 | Masuda |
| 7,770,722 B2 | 8/2010 | Donahoe et al. |
| 7,770,775 B2 | 8/2010 | Shelton et al. |
| 7,776,037 B2 | 8/2010 | Odom |
| 7,780,660 B2 | 8/2010 | Bourne et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,922,063 B2 | 4/2011 | Zemlok et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,251,994 B2 | 8/2012 | McKenna et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,564,242 B2 | 10/2013 | Hansford et al. |
| 8,574,253 B2* | 11/2013 | Gruber et al. ................ 606/171 |
| 8,617,077 B2 | 12/2013 | van Groningen et al. |
| 8,641,629 B2 | 2/2014 | Kurokawa |
| 8,663,112 B2 | 3/2014 | Slayton et al. |
| 8,808,197 B2 | 8/2014 | Videbaek et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2004/0097911 A1 | 5/2004 | Murakami et al. |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton |
| 2005/0171522 A1 | 8/2005 | Christopherson |
| 2005/0256522 A1 | 11/2005 | Francischelli et al. |
| 2006/0030797 A1 | 2/2006 | Zhou et al. |
| 2006/0052774 A1 | 3/2006 | Garrison et al. |
| 2006/0079829 A1 | 4/2006 | Fulton et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0255413 A1 | 10/2008 | Zemlok et al. |
| 2008/0281301 A1 | 11/2008 | Deboer et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0248022 A1* | 10/2009 | Falkenstein et al. ........... 606/51 |

(56) References Cited

U.S. PATENT DOCUMENTS

| | | |
|---|---|---|
| 2009/0253030 A1 | 10/2009 | Kooij |
| 2009/0264940 A1 | 10/2009 | Beale et al. |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0069940 A1 | 3/2010 | Miller et al. |
| 2010/0076455 A1 | 3/2010 | Birkenbach et al. |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0249665 A1 | 9/2010 | Roche |
| 2010/0268221 A1 | 10/2010 | Beller et al. |
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0058982 A1 | 3/2011 | Kaneko et al. |
| 2011/0077514 A1 | 3/2011 | Ulric et al. |
| 2011/0087212 A1 | 4/2011 | Aldridge et al. |
| 2011/0087218 A1 | 4/2011 | Boudreaux et al. |
| 2011/0152901 A1 | 6/2011 | Woodruff et al. |
| 2011/0224668 A1 | 9/2011 | Johnson et al. |
| 2011/0247952 A1 | 10/2011 | Habach et al. |
| 2012/0179036 A1 | 7/2012 | Patrick et al. |
| 2012/0265230 A1 | 10/2012 | Yates et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | EP 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997439 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| JP | 2004-173346 | 6/2004 |
| JP | 2009-096047 | 5/2009 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated Apr. 18, 2012 for Application No. PCT/US2011/059222.
International Search Report dated May 24, 2012 for Application No. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application No. PCT/US2011/059362.
Communication from International Searching Authority dated Feb. 2, 2012 for Application No. PCT/US2011/059222.
Communication from International Searching Authority dated Jan. 24, 2012 for Application No. PCT/US2011/059215.
Communication from International Searching Authority dated Feb. 2, 2012 for Application No. PCT/US2011/059378.
Machine Translation of the Abstract of German Application No. DE 102009013034.
Machine Translation of German Application No. DE 102008051866.
U.S. Appl. No. 13/151,471, filed Jun. 2, 2011, Stulen.
U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,498, filed Jun. 2, 2011, Felder et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/176,875, filed Jul. 6, 2011, Smith et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux et al.
U.S. Appl. No. 13/270,667, filed Oct. 11, 2011, Timm et al.
U.S. Appl. No. 13/270,684, filed Oct. 11, 2011, Madan et al.

(56) References Cited

OTHER PUBLICATIONS

U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, filed Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madan.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, filed Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436. (Abstract).
"System 6 Aseptic Battery System," Stryker (2006) pp. 1-2.
International Search Report dated Jan. 12, 2012 for Application No. PCT/US2011/059226.
International Search Report dated Jan. 26, 2012 for Application No. PCT/US2011/059220.
International Search Report dated Feb. 1, 2012 for Application No. PCT/US2011/059223.
International Search Report dated May 29, 2012 for Application No. PCT/US2011/059358.
International Search Report and Written Opinion dated Jul. 6, 2012 for Application No. PCT/US2011/059381.
Office Action Non-Final dated Aug. 6, 2013 for U.S. Appl. No. 13/151,471.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Jul. 5, 2013 for U.S. Appl. No. 13/151,488.
Office Action Non-Final dated Jun. 14, 2013 for U.S. Appl. No. 13/151,498.
Restriction Requirement dated Mar. 13, 2013 for U.S. Appl. No. 13/151,509.
Restriction Requirement dated Jun. 24, 2013 for U.S. Appl. No. 13/151,509.
Restriction Requirement dated Feb. 28, 2013 for U.S. Appl. No. 13/270,667.
Office Action Non-Final dated Apr. 26, 2013 for U.S. Appl. No. 13/270,667.
Office Action Non-Final dated Dec. 21, 2012 for U.S. Appl. No. 13/274,516.
Office Action Final dated Aug. 16, 2013 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Office Action Final dated Sep. 12, 2013 for U.S. Appl. No. 13/274,805.
Restriction Requirement dated Apr. 29, 2013 for U.S. Appl. No. 13/274,830.
Office Action Non-Final dated Jun. 14, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Office Action Final dated Aug. 29, 2013 for U.S. Appl. No. 13/275,563.
Restriction Requirement dated Feb. 6, 2013 for U.S. Appl. No. 13/276,660.
Office Action Non-Final dated Jun. 3, 2013 for U.S. Appl. No. 13/276,660.
Office Action Non-Final dated Dec. 21, 2012 for U.S. Appl. No. 13/276,673.
Office Action Non-Final dated Aug. 19, 2013 for U.S. Appl. No. 13/276,673.
Restriction Requirement dated Feb. 6, 2013 for U.S. Appl. No. 13/276,687.
Office Action Non-Final dated Jun. 12, 2013 for U.S. Appl. No. 13/276,687.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
US Office Action, Notice of Allowance, dated Nov. 21, 2014 for U.S. Appl. No. 13/151,471.
US Office Action, Notice of Allowance, dated Nov. 21, 2014 for U.S. Appl. No. 13/151,498.
US Office Action, Notice of Allowance, dated Dec. 17, 2014 for U.S. Appl. No. 13/270,667.
US Office Action, Non-Final, dated Dec. 16, 2014 for U.S. Appl. No. 13/270,701.
US Office Action, Notice of Allowance, dated Nov. 28, 2014 for U.S. Appl. No. 13/274,805.
US Office Action, Notice of Allowance, dated Dec. 19, 2014 for U.S. Appl. No. 13/276,745.
US Office Action, Non-Final, dated Dec. 8, 2014 for U.S. Appl. No. 13/277,328.
US Office Action, Non-Final, dated Nov. 7, 2014 for U.S. Appl. No. 13/151,488.
US Office Action, Non-Final, dated Nov. 6, 2014 for U.S. Appl. No. 13/151,503.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.
US Office Action, Non-Final, dated Oct. 22, 2014 for U.S. Appl. No. 13/274,830.
US Office Action, Non-Final, dated Oct. 23, 2014 for U.S. Appl. No. 13/275,563.
European Communication dated Feb. 19, 2014 for Application No. EP 11781972.2.
International Preliminary Report on Patentability for Application No. PCT/US2011/059212 dated May 7, 2013.
International Preliminary Report on Patentability for Application No. PCT/US2011/059215 dated May 8, 2013.
International Preliminary Report on Patentability for Application No. PCT/US2011/059217 dated May 7, 2013.
International Preliminary Report on Patentability for Application No. PCT/US2011/059218 dated May 7, 2013.
International Preliminary Report on Patentability for Application No. PCT/US2011/059220 dated May 7, 2013.
International Preliminary Report on Patentability for Application No. PCT/US2011/059222 dated May 7, 2013.
International Preliminary Report on Patentability for Application No. PCT/US2011/059223 dated May 7, 2013.

(56) References Cited

OTHER PUBLICATIONS

International Preliminary Report on Patentability for Application No. PCT/US2011/059226 dated May 7, 2013.
International Preliminary Report on Patentability for Application No. PCT/US2011/059338 dated May 7, 2013.
International Preliminary Report on Patentability for Application No. PCT/US2011/059351 dated May 7, 2013.
International Preliminary Report on Patentability for Application No. PCT/US2011/059354 dated May 7, 2013.
International Preliminary Report on Patentability for Application No. PCT/US2011/059358 dated May 7, 2013.
International Preliminary Report on Patentability for Application No. PCT/US2011/059362 dated May 7, 2013.
International Preliminary Report on Patentability for Application No. PCT/US2011/059365 dated May 8, 2013.
International Preliminary Report on Patentability for Application No. PCT/US2011/059371 dated May 7, 2013.
International Preliminary Report on Patentability for Application No. PCT/US2011/059378 dated May 7, 2013.
1 International Preliminary Report on Patentability for Application No. PCT/US2011/059381 dated May 8, 2013.
Office Action Non-Final dated Mar. 28, 2014 for U.S. Appl. No. 13/151,471.
Office Action Non Final dated Mar. 18, 2014 for U.S. Appl. No. 13/151,498.
Office Action Non Final dated Jun. 18, 2014 for U.S. Appl. No. 13/151,503.
Office Action Final dated Jan. 29, 2014 for U.S. Appl. No. 13/151,509.
Restriction Requirement dated Jun. 11, 2014 for U.S. Appl. No. 13/151,512.
Office Action Non-Final dated Feb. 14, 2014 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Final dated May 15, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Office Action Final dated Jun. 12, 2014 for U.S. Appl. No. 13/274,516.
Office Action Non-Final dated Jan. 6, 2014 for U.S. Appl. No. 13/275,514.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.
Notice of Allowance dated Dec. 6, 2013 for U.S. Appl. No. 13/151,471.
Office Action Final dated Nov. 21, 2013 for U.S. Appl. No. 13/151,498.
Office Action Non-Final dated Sep. 26, 2013 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Office Action Non-Final dated Dec. 6, 2013 for U.S. Appl. No. 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Notice of Allowance dated Nov. 12, 2013 for U.S. Appl. No. 13/276,687.
Office Action Final dated Nov. 8, 2013 for U.S. Appl. No. 13/276,745.
US Office Action, Notice of Allowance, dated Aug. 19, 2014 for U.S. Appl. No. 13/151,471.
US Office Action, Non-Final, dated Aug. 14, 2014 for U.S. Appl. No. 13/151,481.
US Office Action, Notice of Allowance, dated Aug. 6, 2014 for U.S. Appl. No. 13/151,498.
US Office Action, Non-Final, dated Jul. 9, 2014 for U.S. Appl. No. 13/151,509.
US Office Action, Restriction Requirement, dated Jul. 11, 2014 for U.S. Appl. No. 13/269,780.
US Office Action, Non-Final, dated Jul. 29, 2014 for U.S. Appl. No. 13/270,667.
US Office Action, Restriction Requirement, dated Sep. 11, 2014 for U.S. Appl. No. 13/270,701.
US Office Action, Restriction Requirement, dated Sep. 25, 2014 for U.S. Appl. No. 13/271,352.
US Office Action, Restriction Requirement, dated Jul. 9, 2014 for U.S. Appl. No. 13/270,684.
US Office Action, Non Final, dated Oct. 9, 2014 for U.S. Appl. No. 13/270,684.
US Office Action, Restriction Requirement, dated Oct. 2, 2013 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Restriction Requirement, dated Jul. 9, 2014 for U.S. Appl. No. 13/276,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.
Chinese Office Action dated Jun. 4, 2015 for Application No. 2011800641467.
Chinese Office Action dated Apr. 3, 2016 for Application No. 2011800641467.
Japanese Office Action, Notification of Reasons for Refusal, dated Oct. 27, 2015 for Application No. 2013-537874.
Japanese Office Action, Notification of Reasons for Refusal, dated Jun. 14, 2016 for Application No. 2013-537874.

\* cited by examiner

SELECTIVE ACTIVATION OF ELECTRONIC COMPONENTS IN MEDICAL DEVICE

PRIORITY

This application claims priority to U.S. Provisional Application Ser. No. 61/410,603, filed Nov. 5, 2010, entitled "Energy-Based Surgical Instruments," the disclosure of which is incorporated by reference herein. This application also claims priority to U.S. Provisional Application Ser. No. 61/487,846, filed May 19, 2011, entitled "Energy-Based Surgical Instruments," the disclosure of which is incorporated by reference herein.

BACKGROUND

In some settings, endoscopic surgical instruments may be preferred over traditional open surgical instruments since a smaller incision may reduce the post-operative recovery time and complications. Consequently, some endoscopic surgical instruments may be suitable for placement of a distal end effector at a desired surgical site through a cannula of a trocar. These distal end effectors may engage tissue in a number of ways to achieve a diagnostic or therapeutic effect (e.g., endocutter, grasper, cutter, stapler, clip applier, access device, drug/gene therapy delivery device, and energy delivery device using ultrasound, RF, laser, etc.). Endoscopic surgical instruments may include a shaft between the end effector and a handle portion, which is manipulated by the clinician. Such a shaft may enable insertion to a desired depth and rotation about the longitudinal axis of the shaft, thereby facilitating positioning of the end effector within the patient.

Examples of endoscopic surgical instruments include those disclosed in U.S. Pat. Pub. No. 2006/0079874, entitled "Tissue Pad Use with an Ultrasonic Surgical Instrument," published Apr. 13, 2006, the disclosure of which is incorporated by reference herein; U.S. Pat. Pub. No. 2007/0191713, entitled "Ultrasonic Device for Cutting and Coagulating," published Aug. 16, 2007, the disclosure of which is incorporated by reference herein; U.S. Pat. Pub. No. 2007/0282333, entitled "Ultrasonic Waveguide and Blade," published Dec. 6, 2007, the disclosure of which is incorporated by reference herein; U.S. Pat. Pub. No. 2008/0200940, entitled "Ultrasonic Device for Cutting and Coagulating," published Aug. 21, 2008, the disclosure of which is incorporated by reference herein; U.S. Pat. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; and U.S. Pat. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein. Additionally, such surgical tools may include a cordless transducer such as that disclosed in U.S. Pat. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein. In addition, the surgical instruments may be used, or adapted for use, in robotic-assisted surgery settings such as that disclosed in U.S. Pat. No. 6,783,524, entitled "Robotic Surgical Tool with Ultrasound Cauterizing and Cutting Instrument," issued Aug. 31, 2004, the disclosure of which is incorporated by reference herein.

While several systems and methods have been made and used for surgical instruments, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

Figure 1:
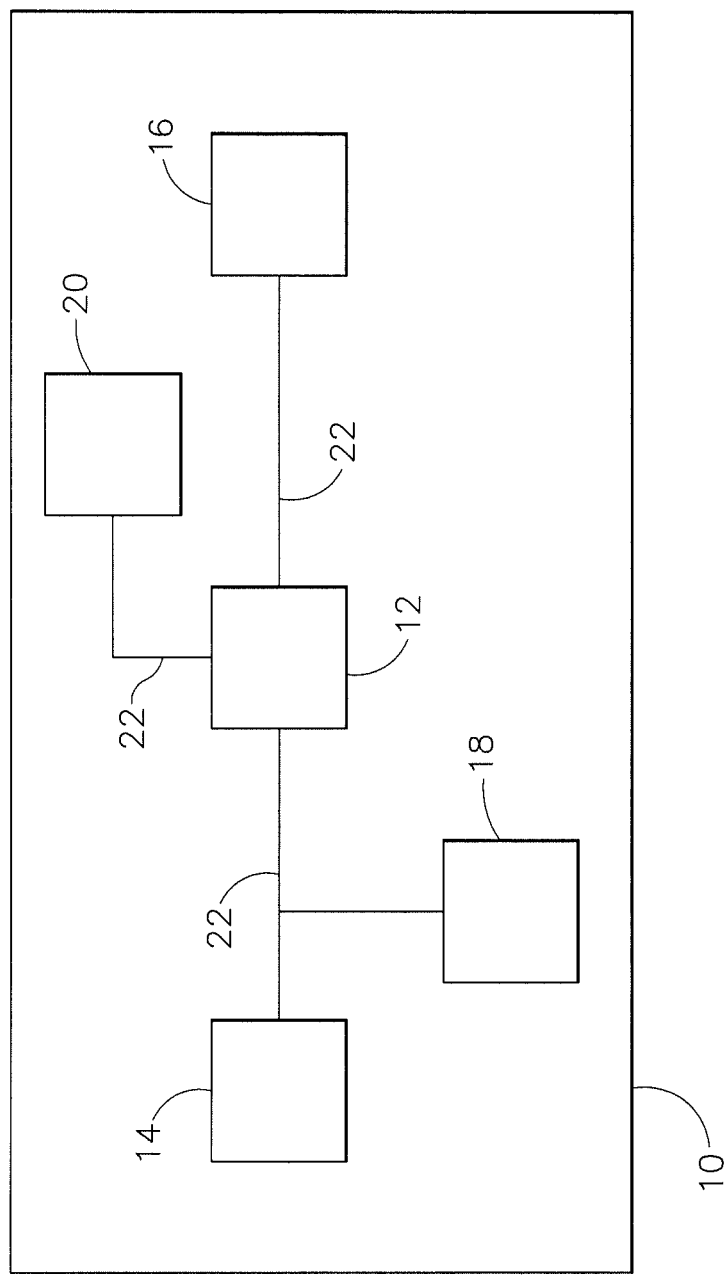
FIG. 1 depicts a schematic view of an exemplary medical device having an internal power source.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

I. Medical Devices for Use With Insertable or Reclaimable Components

FIG. 1 shows components of an exemplary medical device (10) in diagrammatic block form. As shown, medical device (10) comprises a control module (12), a power source (14), and an end effector (16). Merely exemplary power sources (14) may include NiMH batteries, Li-ion batteries (e.g., prismatic cell type lithium ion batteries, etc.), Ni-Cad batteries, or any other type of power source as may be apparent to one of ordinary skill in the art in light of the teachings herein. Control module (12) may comprise a microprocessor, an application specific integrated circuit (ASIC), memory, a printed circuit board (PCB), a storage device (such as a solid state drive or hard disk), firmware, software, or any other suitable control module components as will be apparent to one of ordinary skill in the art in light of the teachings herein. Control module (12) and power source (14) are coupled by an electrical connection (22), such as a cable and/or traces in a circuit board, etc., to transfer power from power source (14) to control module (12). Alternatively, power source (14) may be selectively coupled to control module (12). This allows power source (14) to be detached and removed from medical device (10), which may further allow power source (14) to be readily recharged or reclaimed for resterilization and reuse, such as in accordance with the various teachings herein. In addition or in the alternative, control module (12) may be removed for servicing, testing, replacement, or any other purpose as will be apparent to one of ordinary skill in the art in view of the teachings herein.

End effector (16) is coupled to control module (12) by another electrical connection (22). End effector (16) is configured to perform a desired function of medical device (10). By way of example only, such function may include cauterizing tissue, ablating tissue, severing tissue, ultrasonically vibrating, stapling tissue, or any other desired task for medical device (10). End effector (16) may thus include an active feature such as an ultrasonic blade, a pair of clamping jaws, a sharp knife, a staple driving assembly, a monopolar RF electrode, a pair of bipolar RF electrodes, a thermal heating element, and/or various other components. End effector (16) may also be removable from medical device (10) for servicing, testing, replacement, or any other purpose as will be apparent to one of ordinary skill in the art in view of the teachings herein. In some versions, end effector (16) is modular such that medical device (10) may be used with different kinds of end effectors (e.g., as taught in U.S. Provisional Application Ser. No. 61/410,603, etc.). Various other configurations of end effector (16) may be provided for a variety of different functions depending upon the purpose of medical device (10) as will be apparent to those of ordinary skill in the art in view of the teachings herein. Similarly, other types of components of a medical device (10) that may receive power from power source (14) will be apparent to those of ordinary skill in the art in view of the teachings herein.

Medical device (10) of the present example includes a trigger (18) and a sensor (20), though it should be understood that such components are merely optional. Trigger (18) is coupled to control module (12) and power source (14) by electrical connection (22). Trigger (18) may be configured to selectively provide power from power source (14) to end effector (16) (and/or to some other component of medical device (10)) to activate medical device (10) when performing a procedure. Sensor (20) is also coupled to control module (12) by an electrical connection (22) and may be configured to provide a variety of information to control module (12) during a procedure. By way of example only, such configurations may include sensing a temperature at end effector (16) or determining the oscillation rate of end effector (16). Data from sensor (20) may be processed by control module (12) to effect the delivery of power to end effector (16) (e.g., in a feedback loop, etc.). Various other configurations of sensor (20) may be provided depending upon the purpose of medical device (10) as will be apparent to those of ordinary skill in the art in view of the teachings herein. Of course, as with other components described herein, medical device (10) may have more than one sensor (20), or sensor (20) may simply be omitted if desired.

Figure 2:
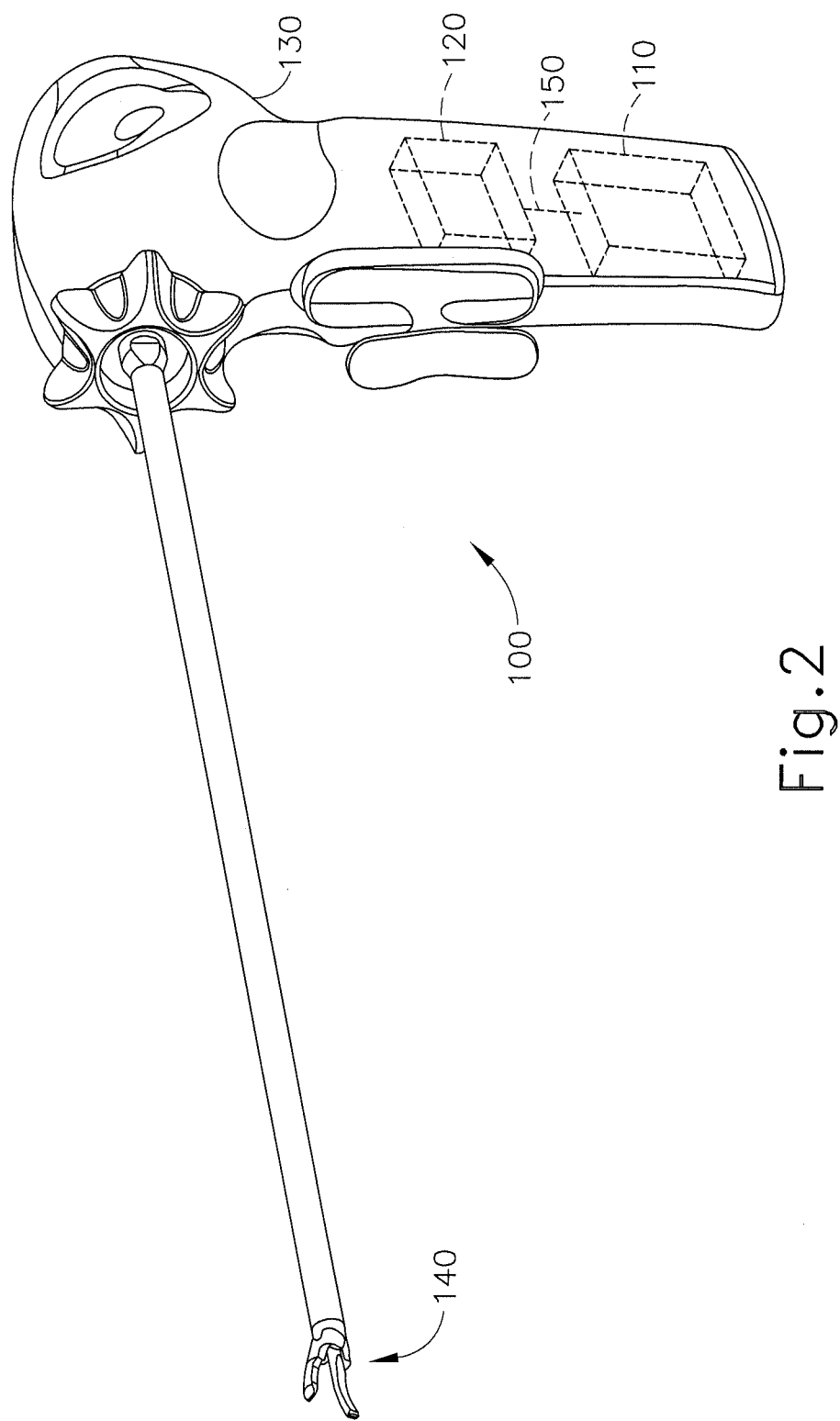
FIG. 2 depicts a perspective view of an exemplary medical device having an internal power source.

FIG. 2 depicts a merely exemplary form that medical device (10) may take. In particular, FIG. 2 shows a medical device (100) comprising a power source (110), a control module (120), a housing (130), end effector (140), and an electrical connection (150). In the present example, power source (110) is located internally within housing (130) of medical device (100). Alternatively, power source (110) may only partially extend into housing (130) and may be selectively attachable to a portion of housing (130). In yet a further exemplary configuration, a portion of housing (130) may extend into power source (110) and power source (110) may be selectively attachable to the portion of housing (130). Power source (110) may also be configured to detach from medical device (100) and decouple from control module (120) or electrical connection (150). As a result, power source (110) may be completely separated from medical device (100) in some versions. By way of example only, power source (110) may be constructed in accordance with the teachings of U.S. Pub. No. 2011/0087212, entitled "Surgical Generator for Ultrasonic and Electrosurgical Devices," published Apr. 14, 2011, now U.S. Pat. No. 8,986,302, issued Mar. 24, 2015, the disclosure of which is incorporated by reference herein. In some versions, power source (110) may be removed to be recharged or reclaimed for resterilization and reuse, such as in accordance with various teachings herein. After recharging, or after an initial charge, power source (110) may be inserted or reinserted into medical device (100) and secured to housing (130) or internally within housing (130). Of course, medical device (100) may also allow power source (110) to be charged and/or recharged while power source (110) is still in or otherwise coupled relative to housing (130).

It should also be understood that control module (120) may be removed for servicing, testing, replacement, or any other purpose as will be apparent to one of ordinary skill in the art in view of the teachings herein. Further, end effector (140) may also be removable from medical device (100) for servicing, testing, replacement, or any other purpose as will be apparent to one of ordinary skill in the art in view of the teachings herein.

While certain configurations of an exemplary medical device (100) have been described, various other ways in which medical device (100) may be configured will be apparent to those of ordinary skill in the art in view of the teachings herein. By way of example only, medical devices (10, 100) and/or any other medical device referred to herein may be constructed in accordance with at least some of the teachings of U.S. Pat. No. 5,322,055 entitled "Clamp Coagulator/Cutting System for Ultrasonic Surgical Instruments," issued Jun. 21, 1994, the disclosure of which is incorporated by reference herein; U.S. Pat. No. 5,873,873 entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811 entitled "Blades with Functional Balance Asymmetries for use with Ultrasonic Surgical Instruments," issued Dec. 4, 2001, the disclosure of which is incorporated by reference herein; U.S. Pub. No. 2006/0079874 entitled "Tissue Pad for Use with an Ultrasonic Surgical Instrument," published Apr. 13, 2006, the disclosure of which is incorporated by reference herein; U.S. Pub. No. 2007/0191713 entitled "Ultrasonic Device for Cutting and Coagulating," published Aug. 16, 2007, the disclosure of which is incorporated by reference herein; U.S. Pub. No. 2007/0282333 entitled "Ultrasonic Waveguide and Blade," published Dec. 6, 2007, the disclosure of which is incorporated by reference herein; U.S. Pub. No. 2008/0200940 entitled "Ultrasonic Device for Cutting and Coagulating," published Aug. 21, 2008, the disclosure of which is incorporated by reference herein; U.S. Pub. No. 2009/0143797, entitled "Cordless Hand-held Ultrasonic Cautery Cutting Device," published Jun. 4, 2009, now U.S. Pat. No. 8,419,757, issued Apr. 16, 2013, the disclosure of which is incorporated by reference herein; U.S. Pub. No. 2010/0069940 entitled "Ultrasonic Device for Fingertip Control," published Mar. 18, 2010, now U.S. Pat. No. 9,023,071, issued May 5, 2015, the disclosure of which is incorporated by reference herein; U.S. Pub. No. 2011/0015660, entitled "Rotating Transducer Mount for Ultrasonic Surgical Instruments," published Jan. 20, 2011, now U.S. Pat. No. 8,461,744, issued Jun. 11, 2013, the disclosure of which is incorporated by reference herein; and/or U.S. Provisional Application Ser. No. 61/410,603, filed Nov. 5, 2010, entitled "Energy-Based Surgical Instruments," the disclosure of which is incorporated by reference herein.

Of course, housing (130) and medical device (100) may include other configurations. For instance, housing (130) and/or medical device (100) may include a tissue cutting element and one or more elements that transmit bipolar RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201, entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein; U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; and U.S. patent application Ser. No. 13/151,481, entitled "Motor Driven Electrosurgical Device with Mechanical and Electrical Feedback," filed Jun. 2, 2011, now U.S. Pat. No. 9,161,803, issued Oct. 20, 2015, the disclosure of which is incorporated by reference herein.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

II. Exemplary Power Delivery Switches

It will be appreciated that in some cases, surgical instrument (50) may be operable in a tether-less mode where an internal power source is used to power surgical instrument (50) rather than plugging surgical instrument (50) into a wall outlet or other external power source. It will also be appreciated that even if surgical instrument (50) is plugged into an outlet, an internal power source may still be used to supplement the externally provided power. It will further be appreciated that an internal power source may lose power or charge simply by being connected to a circuit or other electronics components within surgical instrument (50). Thus, it will be understood that it may be desirable to prevent an internal power source from being connected to a circuit or other electronics prior to actual use of surgical instrument (50) in a surgical operation. Various examples described below include features that reduce the time that a power source is connected to a circuit before use of a surgical instrument in a procedure. It should be understood that the below teachings may be readily incorporated into the various medical devices (10, 100) described above.

Figure 3:
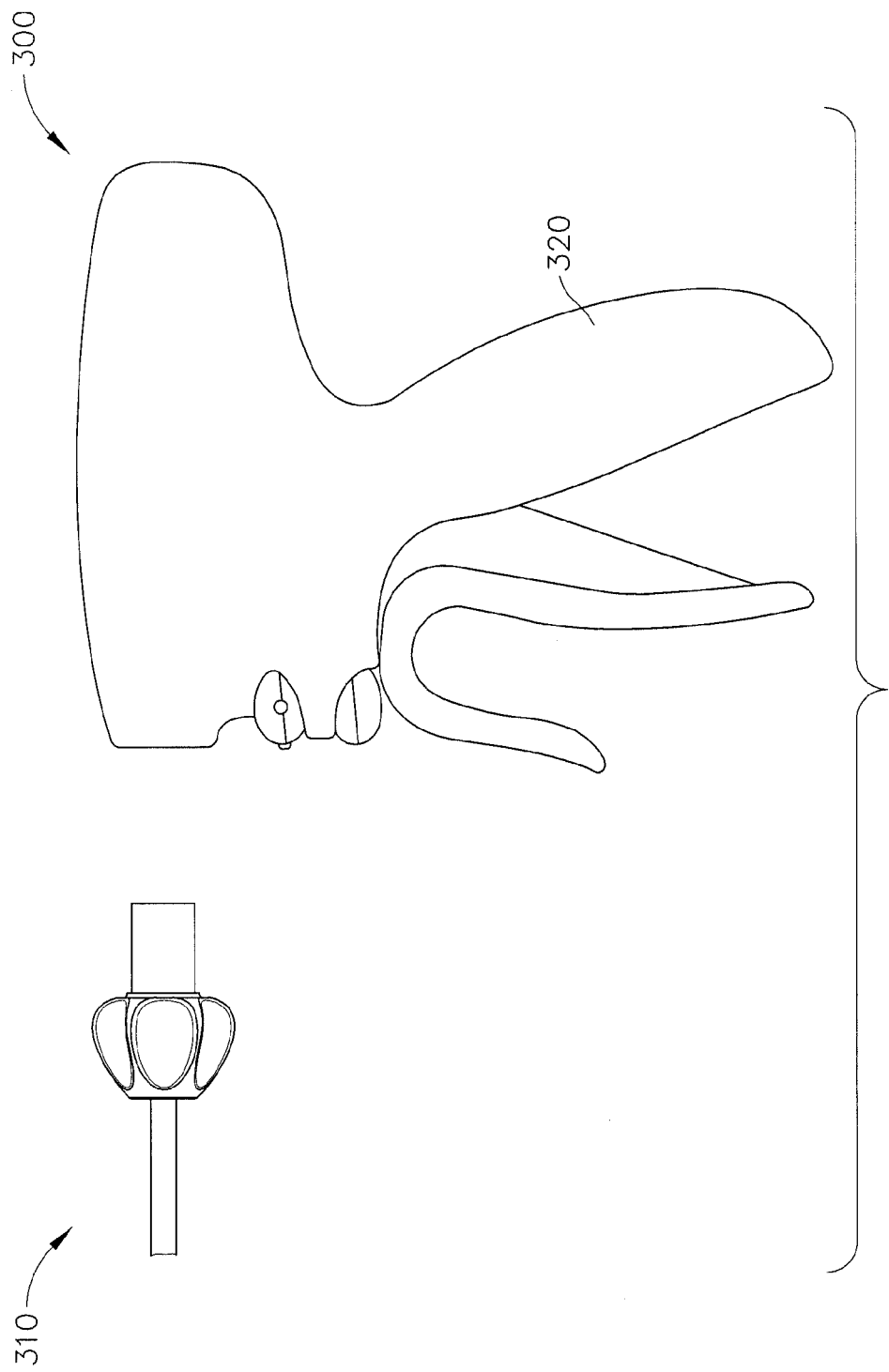
FIG. 3 depicts a side view of an exemplary surgical instrument with a detached transmission assembly.
Figure 4:
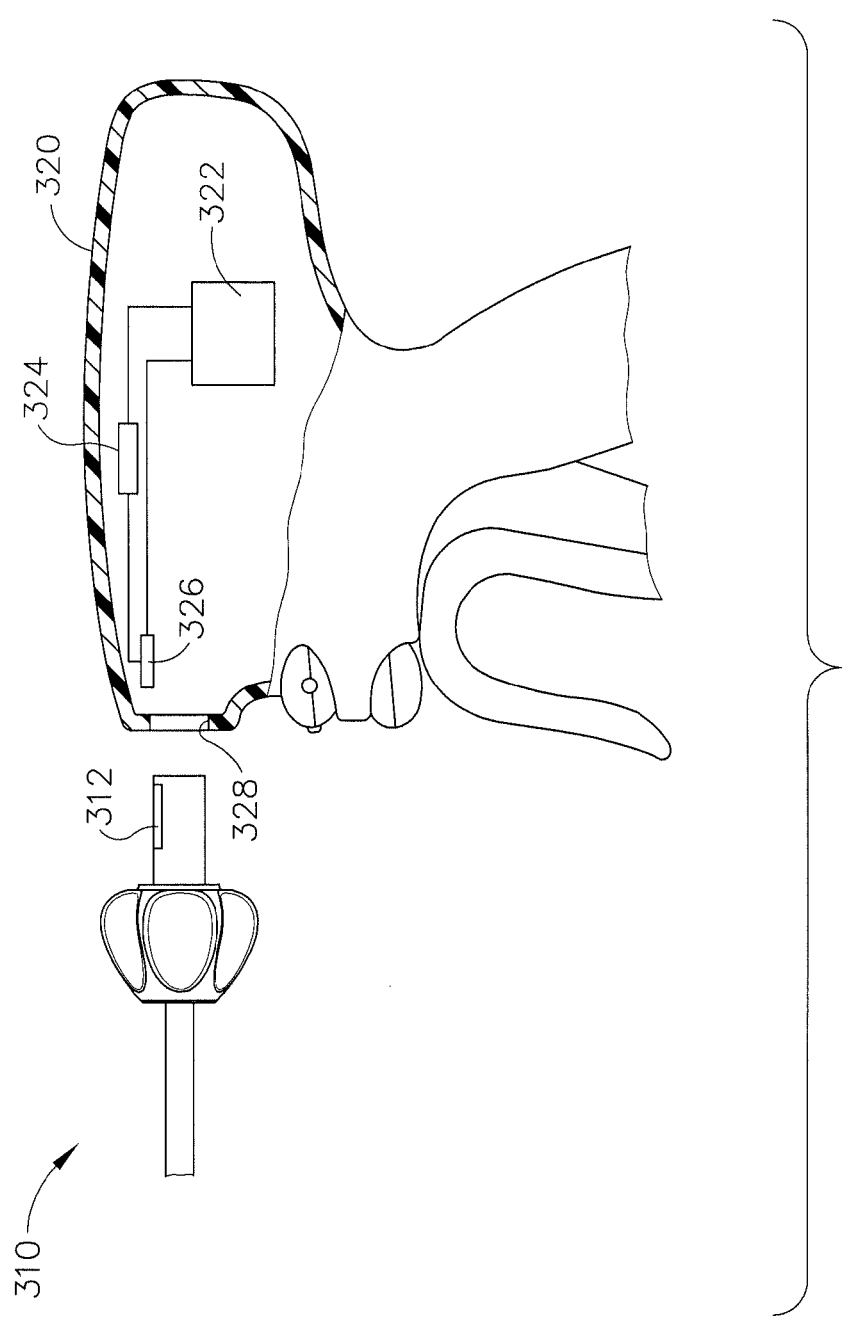
FIG. 4 depicts a side, cross sectional view of the surgical instrument of FIG. 3.

FIG. 3 shows an exemplary surgical instrument (300) with a transmission assembly (310) to be connected to surgical instrument (300). Surgical instrument (300) comprises a handle assembly (320) having an internal power source (322) contained therein, as shown in FIG. 4. In the present example, internal power source (322) comprises a battery, but in other exemplary versions, internal power source (322)

may comprise a rechargeable battery, fuel cell, super capacitor, or any other suitable power source as would be apparent to one of ordinary skill in the art in view of the teachings herein.

An end effector (not shown) is positioned at the distal end of transmission assembly (310). The end effector may include a harmonic blade, RF electrosurgical electrodes, and/or various other components that may be activated by power source (322). Transmission assembly (310) further comprises a magnet (312) positioned on the outer surface of the proximal end of transmission assembly (310). Magnet (312) is further positioned such that once transmission assembly (310) is placed in communication with opening (328), magnet (312) extends proximally into handle assembly (320).

In addition to internal power source (322), handle assembly (320) comprises a switch (326) and control board (324) where switch (326) and control board (324) are in communication with internal power source (322). Switch (326) is located at the distal end of handle assembly (320) such that when transmission assembly (310) is inserted into opening (328), magnet (312) is operable to establish communication with switch (326).

Control board (324) may comprise various electronics and/or circuits operable to control the operation of surgical device (300). It will be appreciated that control board (324) may be operable to control any suitable functionality of surgical device (300) as would be apparent to one of ordinary skill in the art in view of the teachings herein. In some other exemplary versions, it will be appreciated that control board (324) may comprise a timeout timer operable to detect activity of control board (324). In the event that activity in control board (324) is not detected for a predetermined period of time, the timeout timer of control board (324) is operable to effectively shut down control board (324), thereby preventing further drawing of power from internal power source (322). Attempts by the user to once again use surgical device (300) awaken control board (324) and surgical device (300) such that surgical device (300) may be used again.

Switch (326) in the exemplary versions comprises a magnetic switch switchable between a triggered and an untriggered state. In the untriggered state, switch (326) creates an open circuit, thereby preventing power from being delivered from internal power source (322) to control board (324). In the triggered state, switch (326) closes the circuit causing power to be delivered from power source (322) to control board (324). In the exemplary version, since switch (326) comprises a magnetically trigger-able switch (326), such as a reed switch, switch (326) is triggered by magnet (312) being inserted through opening (328) and triggering switch (326). In other exemplary versions, switch (326) may comprise a light/optically triggered switch or a mechanically triggered switch. As a result of using switch (326) and magnet (312), it will be appreciated that surgical instrument (300) is not effectively powered or in an "on" state until magnet (312) triggers switch (326). Thus, surgical instrument (300) is not effectively powered on until transmission assembly (310) is fully coupled with handle assembly (320). While the present example shows magnet (312) coupled with transmission assembly (310) and switch (326) coupled with handle assembly (320), it will be appreciated that magnet (312) and switch (326) may reverse their positioning such that magnet (312) is coupled with handle assembly (320) and switch (326) is coupled with transmission assembly (310). Other suitable configuration will be apparent to one of ordinary skill in the art in view of the teachings herein. By way of example only, switch (326) may comprise a simple electromechanical push switch that is positioned in the path of an inserted transmission assembly (310). Furthermore, other devices such as coils and/or electromagnets may be used to trigger switch (326). Indeed, any suitable device may be used to trigger switch (326) as would be apparent to one of ordinary skill in the art in view of the teachings herein.

Figure 5:
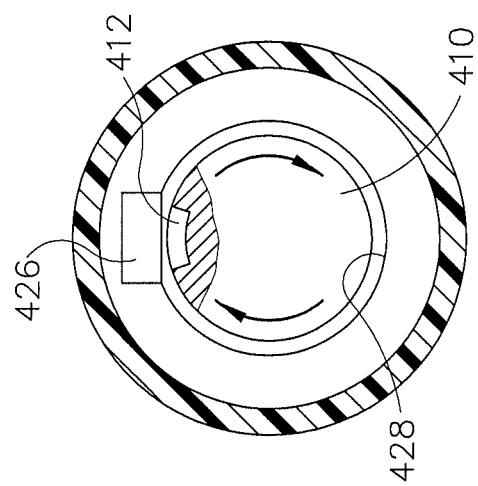
FIG. 5 depicts a front, cross sectional view of an exemplary alternative transmission assembly.
Figure 6:
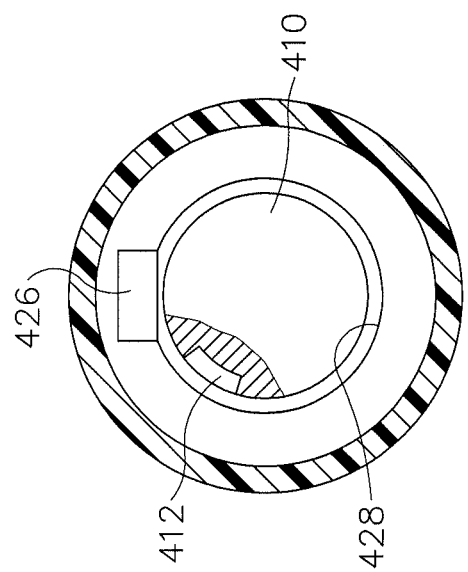
FIG. 6 depicts a front, cross sectional view of the transmission assembly of FIG. 5 after being rotated.
Figure 7:
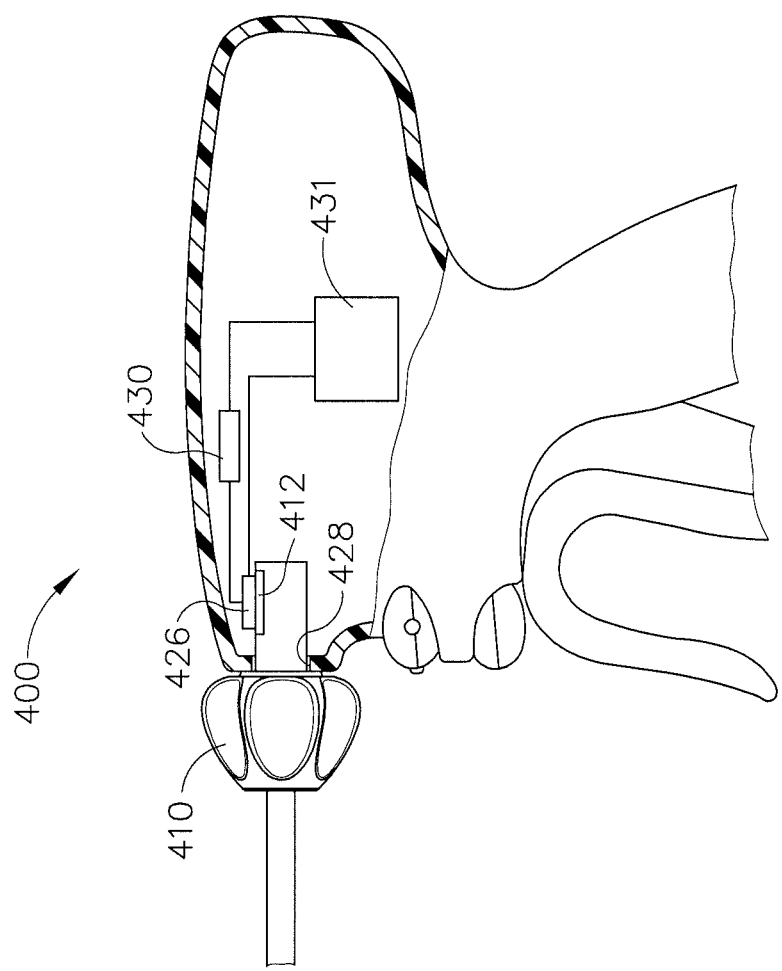
FIG. 7 depicts a side, cross sectional view an exemplary surgical instrument having a secondary switch.

FIGS. 5-7 show an exemplary alternative version of surgical device (400) involving a rotating transmission assembly (410) configuration. A transmission assembly (410) is shown in FIG. 5 inserted into opening (428). Transmission assembly (410) includes a magnet (412) operable to trigger switch (426) by coming in contact and/or close proximity with switch (426). In FIG. 5, transmission assembly (410) has been rotated such that magnet (412) does not trigger switch (426). In some exemplary versions, the configuration shown in FIG. 5 may be the default positional relationship between transmission assembly (410) and switch (426). When the user wishes to use surgical instrument (400), then the user may rotate transmission assembly (410) such that magnet (412) and switch (426) are aligned. It will be appreciated that the rotation of transmission assembly (410) may trigger a mechanical snap or other audible indicator to indicate that transmission assembly (410) has been aligned properly to trigger switch (426) with magnet (412). For instance, transmission assembly (410) and handle assembly (420) may include complementary detent features. It should also be understood that transmission assembly (410) and handle assembly (420) may be coupled through a bayonet mount, such that transmission assembly (410) is rotated to the position shown in FIG. 6 when the bayonet mount is fully seated. In some exemplary versions, as seen in FIG. 7, a secondary switch (430) may be used in communication with switch (426). Secondary switch (430) comprises a permanent switch operable to be triggered by switch (426). It will be appreciated that secondary switch (430) is also operable to close a circuit to power surgical instrument (400). Surgical instrument (400) comprises a power source (431) in communication with switch (426), secondary switch (430), and transmission assembly (410) such that if either switch (426) or secondary switch (430) are closed, power source (431) may transmit power to transmission assembly (410) to ultimately deliver energy or ultrasonic vibrations to an end effector (not shown) at the distal end of transmission assembly (410). As a result, when secondary switch (430) is triggered, even if magnet (412) and switch (426) are no longer aligned, surgical instrument (400) remains powered.

Figure 8:
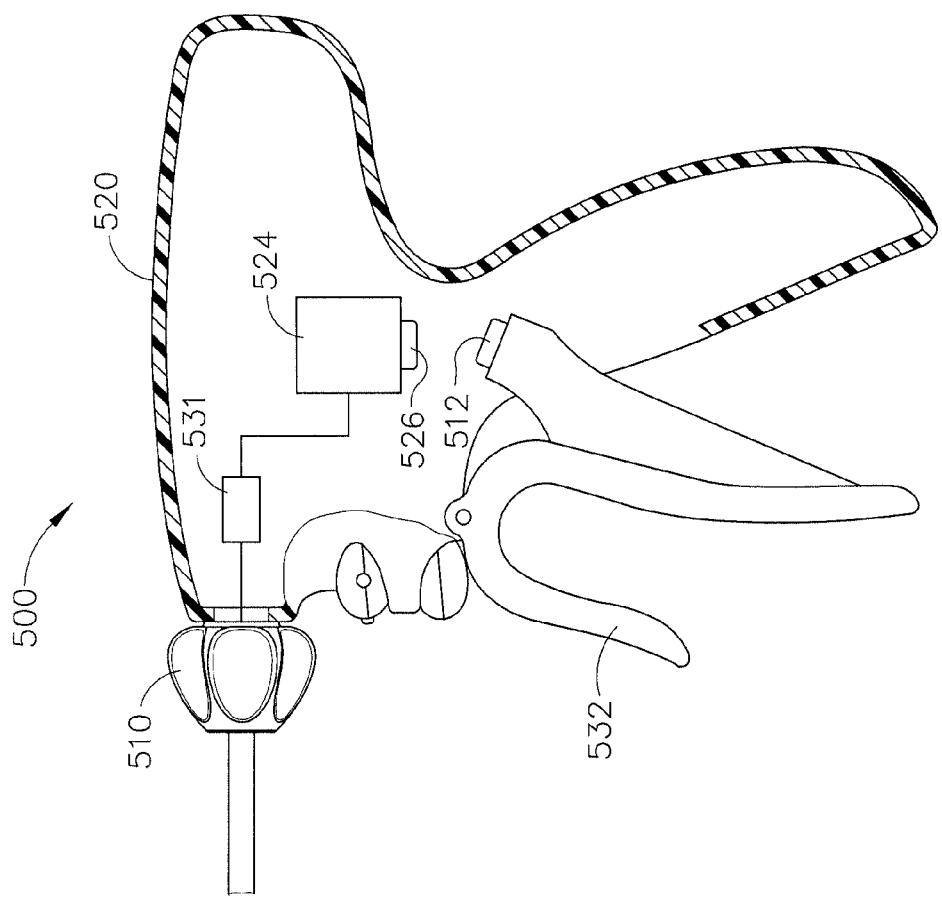
FIG. 8 depicts a side, cross sectional view of an exemplary surgical instrument with a trigger actuatable switch.
Figure 9:
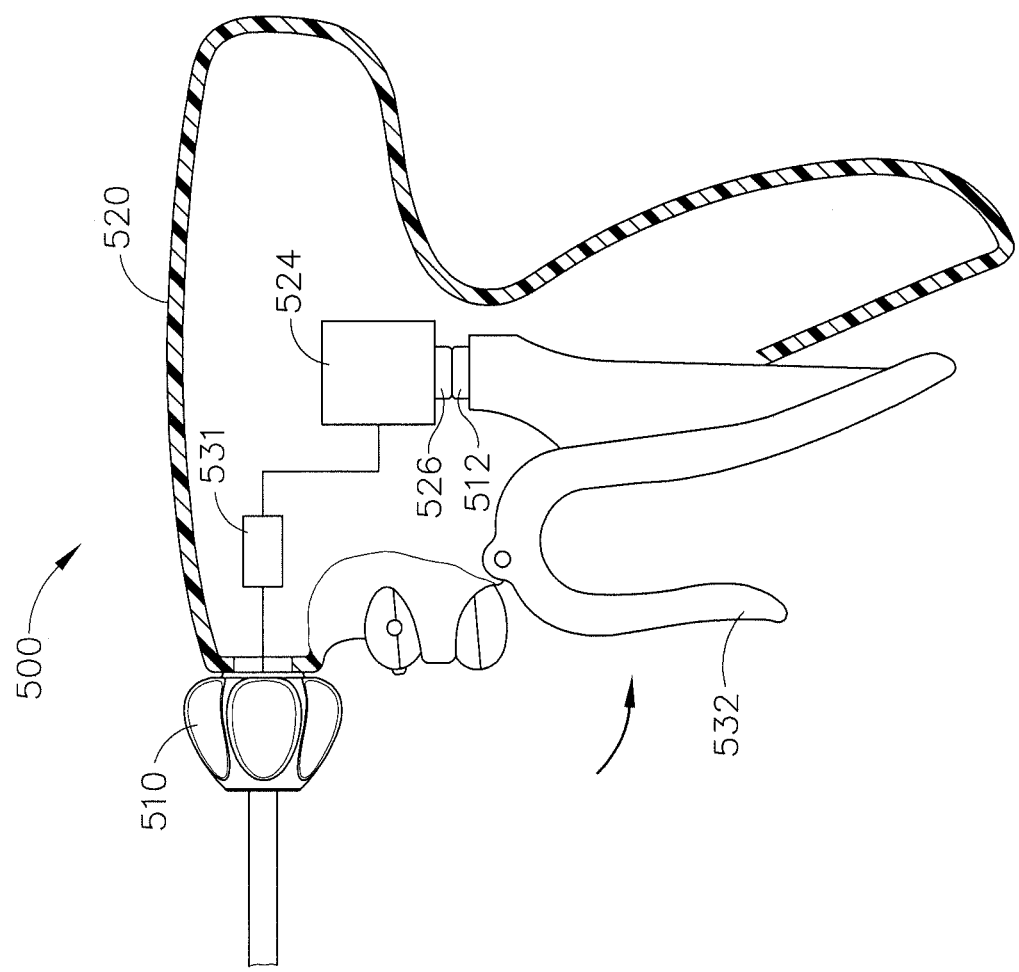
FIG. 9 depicts a side, cross sectional view of the surgical instrument of FIG. 8 with the trigger actuated.

FIG. 8 shows another exemplary version of a surgical instrument (500) having a transmission assembly (510) connected to a handle assembly (520). Handle assembly (520) houses a trigger (532) and control board (524). A magnet (512) is attached to a proximal portion of trigger (532) such that when trigger (532) is actuated by a user as shown in FIG. 9, magnet (512) comes into contact with switch (526) in communication with control board (524). Surgical instrument (500) remains in an unpowered state until switch (526) is triggered by the user. Thus, when the user is ready to use surgical instrument (500), the user may squeeze trigger (532), thereby causing switch (526) to be closed. Surgical instrument (500) comprises a power source (531) in communication with switch (526) and transmission assembly (510) such that if switch (426) is closed, power source (531) may transmit power to transmission assembly (510) to ultimately deliver energy or ultrasonic vibrations to an end effector (not shown) at the distal end of transmission assembly (510). In the present example, switch (526) comprises a reed switch, though it should be understood that any suitable type of switch may be used as would be apparent to one of ordinary skill in the art in view of the teachings herein. It will be appreciated that in some exemplary versions, trigger (532) may be squeezed through a packaging holding surgical instrument (500) prior to removal of instrument (500) from the packaging, thereby allowing user to verify that surgical instrument (500) is in proper working condition prior to removing surgical instrument (500) from packaging and using surgical instrument (500) in a surgical procedure.

Figure 10:
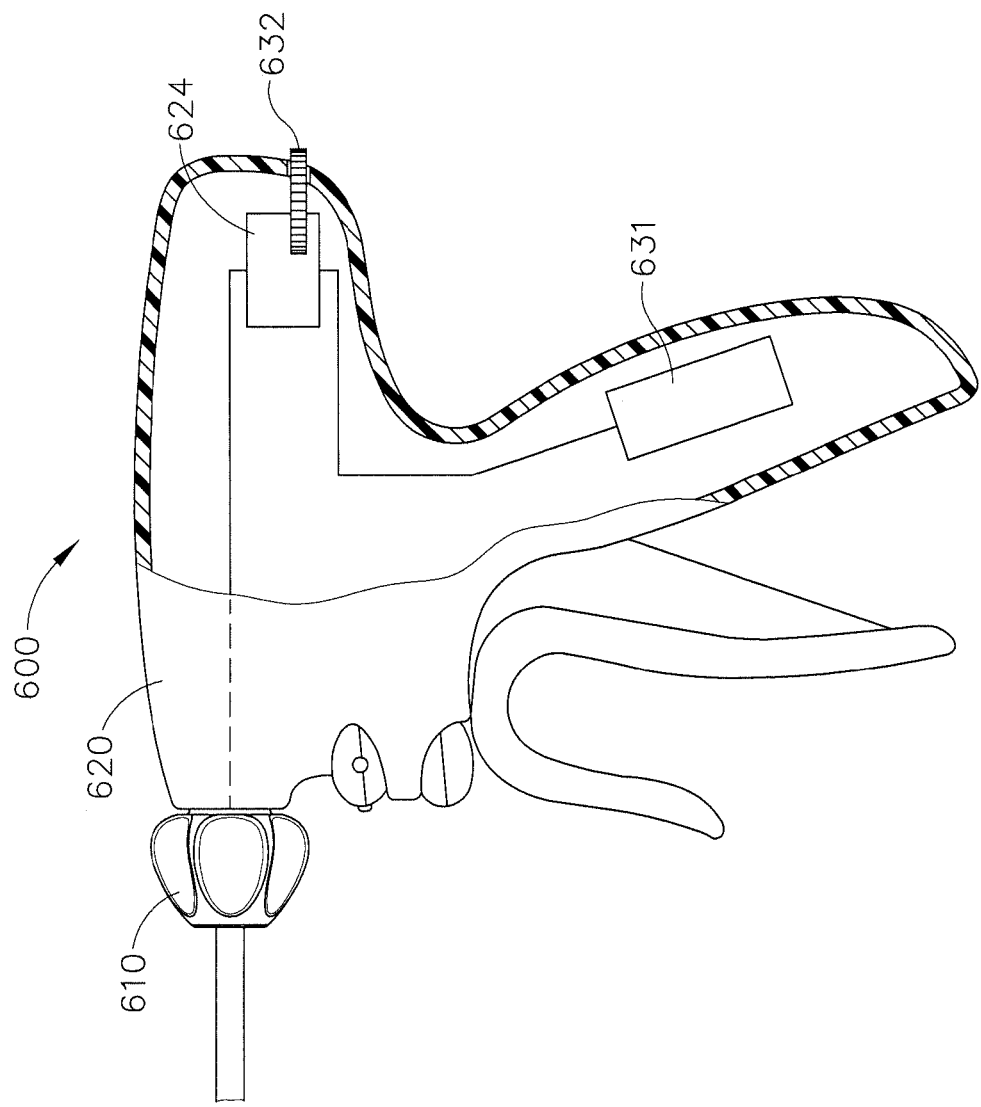
FIG. 10 depicts a side, cross sectional view of an exemplary surgical instrument with a pull tab.

FIG. 10 shows yet another exemplary version of surgical instrument (600) having a transmission assembly (610) and a handle assembly (620). Surgical instrument (600) further comprises a pull tab (632) removably coupled with handle assembly (620). Pull tab (632) comprises an electrically isolated material and is in communication with control board (624). Since pull tab (632) comprises an electrically isolated material, it will be appreciated that pull tab (632) is operable to create an open circuit within control board (624) thereby rendering control board (624) as well as surgical instrument (600) in an unpowered state. Pull tab (632) extends externally outward from surgical instrument (600) such that a user can remove pull tab (632) thereby removing pull tab (632) from control board (624). As a result, the electrically isolated material is removed such that the open circuit in control board (624) becomes closed, thereby causing control board (624) to be powered for operation by power source (631). For instance, a resiliently biased contact associated with control board (264) may bear against pull tab (632), such that the contact engages a complementary contact to complete the circuit once pull tab (632) is removed. In some exemplary versions, pull tab (632) may be integrated to be part of a packaging material storing surgical instrument (600) such that pull tab (632) is removed when surgical instrument (600) is removed from packaging. Once pull tab (632) is removed, power source (631) may deliver power to transmission assembly (610) to deliver energy or ultrasonic vibrations to an end effector (not shown) located at the distal end of transmission assembly (610).

Figure 11:
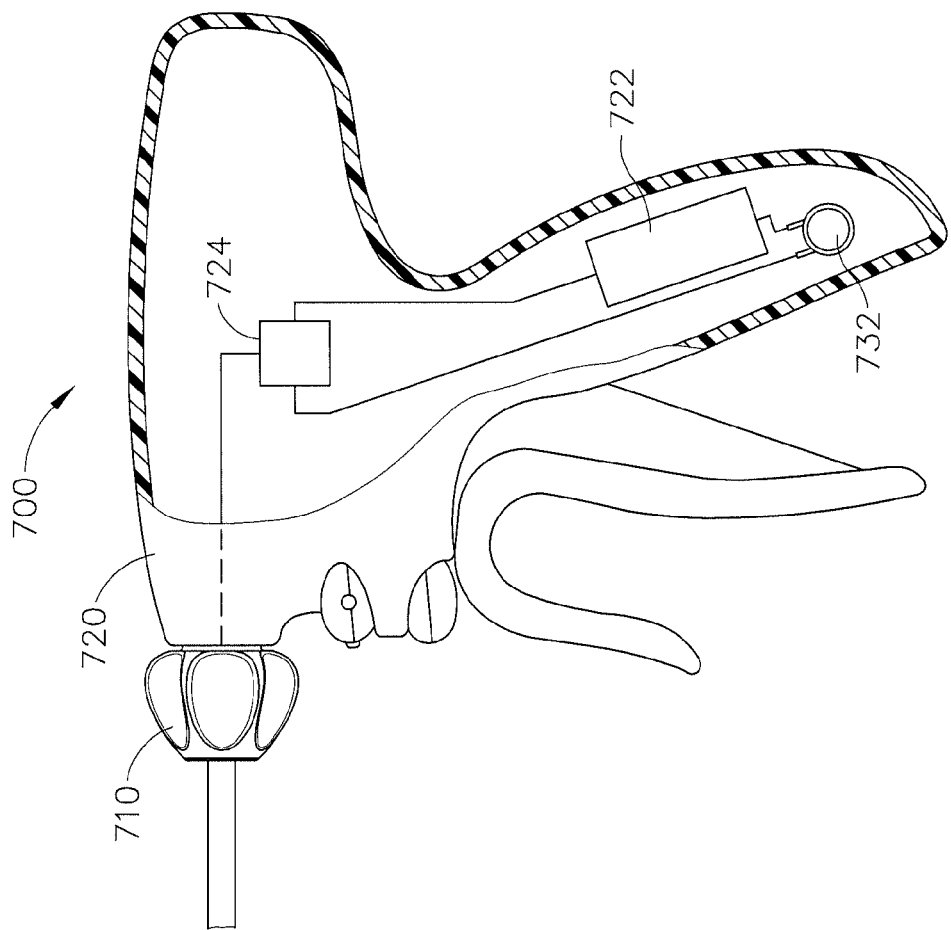
FIG. 11 depicts a side, cross sectional view of an exemplary surgical instrument with a button actuated switch.

FIG. 11 shows an exemplary alternative version of surgical instrument (700) having a transmission assembly (710) and a handle assembly (720). In this example, handle assembly (720) further comprises a user activated button (732). Button (732) is in communication with a control board (724). Control board (724) is in communication with an internal power source (722) operable to power control board (724). Button (732) is operable to act as a switch to wake up surgical instrument (700) such that internal power source (722) can deliver power to control board (724). Thus, when the user is ready to use surgical instrument (700), the user may press button (732) to complete the circuit and begin delivery of power from internal power source (722) to transmission assembly (710) where transmission assembly (710) then delivers ultrasonic vibrations or energy to an end effector (not shown) at the distal end of transmission assembly (710). Button (732) has a shape large enough such that button (732) may be actuated through packaging or other similar material. While the exemplary version comprises a button (732) configuration, it will be appreciated that button (732) may comprise any component that may be actuated such as a toggle switch, a sliding switch, or any other suitable switch as would be apparent to one of ordinary skill in the art in view of the teachings herein.

Figure 12:
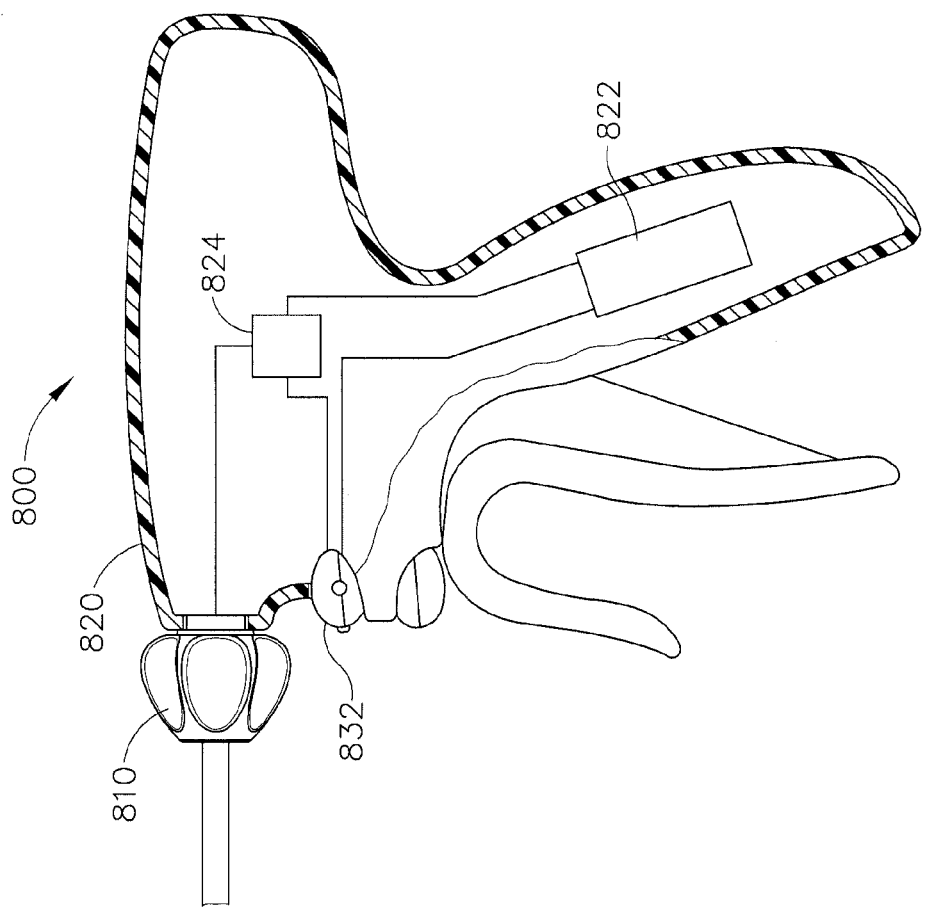
FIG. 12 depicts a side, cross sectional view of an exemplary surgical instrument with a button used as a trigger.

FIG. 12 shows another exemplary alternative version of a surgical instrument (800) having a transmission assembly (810) and a handle assembly (820). In this example, handle assembly (820) comprises a control board (824) in communication with an internal power source (822). A trigger button (832) is positioned to be in communication with control board (824) and internal power source (822). In this example, trigger button (832) is operable to selectively establish electrical communication between control board (824) and internal power source (822). Trigger button (832) may be moveable between an actuated and an unactuated state where trigger button (832) is biased to be in an unactuated state. When user presses trigger button (832), trigger button (832) moves to an actuated state. When in an actuated state, internal power source (822) is connected to control board (824) such that control board (824) is operable to deliver power from power source (822) to transmission assembly (810) where transmission assembly (810) can then deliver ultrasonic vibrations or energy to an end effector (not shown) positioned at the distal end of transmission assembly (810). In the event that the user releases trigger button (832), then the connection between internal power source (822) and control board (824) is broken. In some exemplary versions trigger button (832) may be operable to act as a toggle where a single press connects internal power source (822) to control board (824) and maintains that connection even after trigger button (832) is released; while a second press breaks the connection between internal power source (822) and control board (824). It will be appreciated that once trigger button (832) is depressed, power delivery to control board (824) may occur within 100 ms, or sooner, such that there is no noticeable delay to the user. In other exemplary versions, the delay may be any amount suitable to one of ordinary skill in the art in view of the teachings herein.

Figure 13:
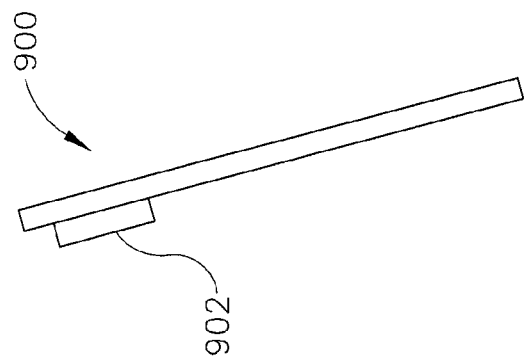
FIG. 13 depicts a side view of an exemplary wand.

FIG. 13 shows an exemplary wand (900) that may be used with, for example, surgical instrument (300, 400, 500) of FIGS. 3-9. Wand (900) comprises a magnet (902) operable to trigger any of the magnetic switches (326, 426, 526) shown in FIGS. 3-9. As a result, rather than pressing a button or performing some other action, the user may wave wand (900) proximate to a magnetic switch (326, 426, 526) to trigger the magnetic switch (326, 426, 526). In some versions, magnet (312, 412, 512) may be omitted from transmission assembly (310, 410) or trigger (532) and the magnet (902) of wand (900) may instead be used to trigger the magnetic switch (326, 426, 526). It will further be appreciated that wand (900) may be used to check the functionality of surgical instrument (300, 400, 500) prior to removing surgical instrument (300, 400, 500) from packaging and/or prior to use of surgical instrument (300, 400, 500) in a surgical procedure. In other words, magnet (902) may provide a magnetic field through packaging of instrument (300, 400, 500) in a manner sufficient to trigger a responsive feature in instrument (300, 400, 500).

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery. For instance, those of ordinary skill in the art will recognize that various teaching herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body having a distal end portion;
   (b) a control unit;
   (c) a power source, wherein the power source is configured to selectively deliver power to the control unit;
   (d) a shaft assembly extending distally from the distal end portion of the body, wherein the shaft assembly includes a proximal portion insertable into the body; and
   (e) a switch in communication with the control unit, wherein the switch is in further communication with the power source, wherein the proximal portion of the shaft assembly is configured to actuate the switch thereagainst, wherein the switch is located in the distal end portion of the body and structurally positioned to be adjacent to the proximal portion of the shaft assembly for actuation thereof, wherein the switch is configured to be actuated by rotational movement of the proximal portion of the shaft assembly against the switch within the body to initiate delivery of power from the power source.

2. The surgical instrument of claim 1, further comprising a magnet in communication with the shaft assembly, wherein the magnet is configured to actuate the switch.

3. The surgical instrument of claim 1, wherein the switch comprises a reed switch.

4. The surgical instrument of claim 1, further comprising a time out timer operable to determine if the control unit is actively being used.

5. The surgical instrument of claim 1, further comprising a secondary switch operable to selectively provide continuous delivery of power to the control unit.

6. The surgical instrument of claim 1, wherein the shaft assembly includes an end effector driven by the power source.

7. The surgical instrument of claim 1, wherein the switch is located at a position in the body such that the switch is structurally positioned to be actuated by movement of the proximal portion of the shaft assembly within the body to initiate delivery of power from the power source to the control unit.

8. An apparatus comprising:
   (a) a surgical instrument operable to be powered by a power source, wherein the surgical instrument is operable to perform an electrically powered surgical procedure, wherein the surgical instrument defines a distally facing opening, wherein the surgical instrument comprises a shaft assembly having a proximal end structurally configured to fit within the distally facing opening and be rigidly secured therein, wherein the proximal end of the shaft assembly further comprises a triggering member;
   (b) a control unit in communication with the surgical instrument, wherein the control unit is configured to receive power from the power source; and
   (c) a switch having a first state and a second state, wherein the switch is structurally positioned to transition from the first state to the second state in response to proximity of the triggering member upon insertion and rigid securement of the proximal end of the shaft assembly in the distally facing opening, wherein the shaft assembly is configured to be rotated within the surgical instrument to actuate the switch.

9. The apparatus of claim 8, wherein the triggering member comprises a magnet configured to actuate the switch.

10. The apparatus of claim 8, wherein the first state comprises an actuated state, wherein the second state comprises an unactuated state.

11. The apparatus of claim 10, wherein the switch is configured to initiate delivery of power from the power source to the control unit when in the actuated state, wherein the switch is configured to completely stop the delivery of power from the power source to the control unit when in the unactuated state.

12. A surgical instrument comprising:
(a) a body;
(b) a control unit;
(c) a power source, wherein the power source is configured to selectively deliver power to the control unit;
(d) a shaft assembly extending distally from the body, wherein the shaft assembly includes a proximal portion insertable into the body; and
(e) a switch in communication with the control unit, wherein the switch is in further communication with the power source, wherein the switch is located at a position in the body such that the switch is structurally positioned to be actuated by movement of the proximal portion of the shaft assembly within the body to initiate delivery of power from the power source,
wherein the shaft assembly is configured to be rotated to actuate the switch.

\* \* \* \* \*